United States Patent
Wong et al.

(10) Patent No.: US 9,428,712 B2
(45) Date of Patent: Aug. 30, 2016

(54) PERFUMING COMPOSITIONS AND USES THEREOF

(71) Applicant: FIRMENICH SA, Geneva (CH)

(72) Inventors: Kenneth Wong, Geneva (CH); Aude Daugeron Jouault, Neuilly sur Seine (FR); Sophie Bonnus, Paris (FR); Rémy Mounier, Aulnay sur Mauldre (FR); Anton Furrer, Confignon (CH); Damien Berthier, Geneva (CH)

(73) Assignee: Firmenich SA, Geneva (CH)

( * ) Notice: Subject to any disclaimer, the term of this patent is extended or adjusted under 35 U.S.C. 154(b) by 125 days.

(21) Appl. No.: 14/356,145

(22) PCT Filed: Oct. 25, 2012

(86) PCT No.: PCT/EP2012/071105
§ 371 (c)(1),
(2) Date: May 2, 2014

(87) PCT Pub. No.: WO2013/064412
PCT Pub. Date: May 10, 2013

(65) Prior Publication Data
US 2014/0287982 A1    Sep. 25, 2014

(30) Foreign Application Priority Data
Nov. 4, 2011    (EP) .................................... 11187948

(51) Int. Cl.
*A61K 8/00*    (2006.01)
*C11B 9/00*    (2006.01)
*A61Q 13/00*    (2006.01)
*A61K 8/39*    (2006.01)

(52) U.S. Cl.
CPC . *C11B 9/00* (2013.01); *A61K 8/39* (2013.01); *A61Q 13/00* (2013.01)

(58) Field of Classification Search
CPC ................................. C11B 9/00; A61Q 13/00
USPC ............................................................ 512/2
See application file for complete search history.

(56) References Cited

U.S. PATENT DOCUMENTS

| 5,409,694 A * | 4/1995 | Meyer ...................... A61K 8/27 424/67 |
| 5,726,345 A | 3/1998 | Paget et al. |
| 6,036,964 A * | 3/2000 | Guenin .................. A61K 8/342 424/401 |
| 6,677,297 B2 | 1/2004 | Frerot |
| 2004/0102357 A1 | 5/2004 | Smith et al. |

FOREIGN PATENT DOCUMENTS

| DE | 30 03 494 A1 | 8/1980 |
| EP | 0 936 211 B1 | 8/1999 |

(Continued)

*Primary Examiner* — Ling Choi
*Assistant Examiner* — Lanee Reuther
(74) *Attorney, Agent, or Firm* — Winston & Strawn LLP

(57) ABSTRACT

The present invention relates to the field of perfumery. More particularly, it provides a perfuming composition capable of prolonging the release of a perfuming component into the surrounding environment when applied on a body surface. The composition comprises PPG-3 myristyl ether as a fragrance evaporation modulator in the presence of high amounts of ethanol. The invention also relates to consumer articles containing such compositions. It finally provides methods for the perfuming of a body surface and a method for increasing the long-lastingness of a perfuming component using these compositions.

17 Claims, 6 Drawing Sheets

(56) References Cited

FOREIGN PATENT DOCUMENTS

| EP | 0 971 021 A1 | 1/2000 |
|---|---|---|
| WO | WO 95/04809 A1 | 2/1995 |
| WO | WO 95/08976 A1 | 4/1995 |
| WO | WO 98/47477 A1 | 10/1998 |
| WO | WO 99/60990 A2 | 12/1999 |
| WO | WO 01/28980 A1 | 4/2001 |
| WO | WO 03/049666 A2 | 6/2003 |
| WO | WO 2008/093272 A2 | 8/2008 |

* cited by examiner

PERFUMING COMPOSITIONS AND USES THEREOF

CROSS-REFERENCE TO RELATED APPLICATIONS

This application is a 371 filing of International Patent Application PCT/EP2012/071105 filed Oct. 25, 2012, which claims the benefit of European application no. 11187948.2 filed Nov. 4, 2011.

TECHNICAL FIELD

The present invention relates to the field of perfumery. More particularly, it provides compositions wherein the release of a particular fragrance is modulated via the use of specific amounts of a modulating agent. The compositions of the invention comprise PPG-3 myristyl ether (PPG=polypropylene glycol) in the presence of high amounts of ethanol. The invention also relates to methods of use of said compositions and to a method for increasing the long-lastingness of a fragrance component using these compositions.

PRIOR ART

In the perfumery industry there is a constant need to find new technologies for prolonging the perception of perfumes over time. Such a need is particularly marked when dealing with perfumes rich in highly volatile compounds which evaporate quickly, such that the fragrance intensity, as perceived by the user and others in his environment, decreases rapidly with time. The perceived extent of this decrease is further enhanced by the rapid evaporation of ethanol, present in high amounts in fragrances and "eaux de toilette" (colognes), as well as in body splashes. Maintaining intensity over time is key for a commercial fragrance. Indeed, consumers look for fragrances that last all day long. It is commonly accepted that a fragrance has to maintain a good intensity for at least 8 hours to satisfy this consumer need, the main challenge being to maintain the intensity of the highly volatile compounds. The present invention aims at providing perfume compositions the top and middle notes of which have an improved intensity over time.

Retarding the evaporation of highly volatile ingredients present in fragrances is therefore one of the main aims of research in fragrance design and creation, and many approaches to solving this problem have been described in the prior art. The use of agents of various nature, capable of modifying the characteristics of evaporation of fragrance ingredients and fragrances, has produced a prior art so vast that it cannot possibly be cited exhaustively here. Such prior disclosed agents range from heavy perfumery materials and perfume extenders (understood to be compounds having an odour, and which are compatible both as to solubility and odour, with a more expensive or less available perfume oil, and, when admixed or used in conjunction therewith, extend the usefulness of the oil), to a large variety of polymeric or gel-like materials capable of forming film-like or structured arrangements such as micelles which trap the perfume, to fragrance encapsulating carrier materials, or yet to the so-called pro-perfumes, i.e. chemical entities which release a perfuming ingredient via chemical degradation or cleavage, when applied to a surface under controlled conditions.

Many prior researchers have proposed the use of so-called "fixatives" but, to the best of our knowledge, such prior art proposals are indiscriminate in relation to the fragrance nature, i.e. they advocate the use of the fixatives with any perfume ingredient or fragrance, assuming that all ingredients are affected in much like the same manner by a certain fixative.

We have now surprisingly established that this is not the case and the present invention provides a different and selective approach, aimed at benefiting from the selection of a modulator of specific nature, PPG-3 myristyl ether, or a fragrance modulator mixture formed thereof, to be used with fragrances which comprise a defined amount of perfume ingredients with specific vapor pressures. We have in fact established that such a solution provides longer lasting fragrances in the cases where prolonging the perception of the fragrance is most needed, whilst still allowing freedom to the perfumer in the choice of perfuming ingredients at his or her disposal to achieve the desired hedonic effect, particularly amongst ingredients in the higher vapor pressure range of the perfumer's palette.

The compositions of the invention are not known from the prior art. Whereas PPG-3 myristyl ether is a polar cosmetic oil with known emollient properties in cosmetic compositions, appreciated for its ability to blend suitably in transparent deodorant/antiperspirant sticks, to act as a slip agent, to the best of our knowledge it has never been reported or suggested for use in retarding evaporation of perfume ingredients and modulating the evaporation profile of specific ranges of more volatile components in fragrances, the latter being typically devoid of fatty-like components. Its use as a modulator of the evaporation profile of fragrances of specific nature is a totally unexpected and advantageous contribution to perfumery technology.

The present invention brings a novel and advantageous solution to the problem of prolonging the long-lastingness of fragrances comprising a significant amount of the most volatile perfuming components, as well as high amounts of ethanol or other alcohols commonly used in commercial perfumes.

DESCRIPTION OF THE INVENTION

The present inventors have surprisingly established that perfumery ingredients can be efficiently released from perfumes containing PPG-3 myristyl ether as a perfume evaporation modulator.

Thus, the invention relates to a composition consisting of:
a) a fragrance component, in an amount of between 3 and 40% by weight of the composition's weight, at least 40% by weight of the total weight of said fragrance component being formed of perfuming ingredients having a calculated vapor pressure V comprised in the range $0.05 \leq V \leq 300$ Pa
b) from 40 to 90% by weight, relative to the total weight of the composition, of ethanol;
c) from 0.01 to 20% by weight, relative to the total weight of the composition, of a fragrance modulator formed of PPG-3 myristyl ether; and
d) optionally water;
and wherein the sum of the weights of ingredients a) to d) adds up to at least 98% of the composition's weight.

By "consisting of" it is meant here that the composition consists essentially of the recited components but may contain small amounts (not more than 2% weight thereof) of other ingredients that do not have an impact on the release of the fragrance component. The composition may for example comprise stabilising or anti-oxidation agents of current use in perfumery, UV filters or quenchers, or yet colouring agents. It will however be devoid of cosmetic ingredients of varied nature, such as emollients, skin softening agents, bactericide agents, antitranspirant salts, deodorant agents, preservatives, skin care actives; moisturizing agents, surfactants, soothing agents, hair fixatives, hair conditioners, skin conditioners, propellants and any other type of substance current is cosmetics, soaps, creams and gels, intended for application to the skin and hair, and which is of a nature susceptible of having an effect on the evaporation rate and release of the fragrance.

Apart from these small amounts of the above ingredients, ingredients a) to d) shall form 98% at least of the total weight of the composition, each of ingredients a) to c) being present in an amount comprised in the respective range cited above. This also means that, when the composition comprises no water, components a) to c) are present in amounts comprised within the respective ranges defined above, in such a way that the total sum of their weights adds up to at least 98% of the total composition weight.

The compositions according to the invention are so-called fine fragrance compositions (perfumes or fragrances), meaning ethanol based compositions, essentially intended to perfume skin or hair, i.e. to impart a pleasant odour thereto, or cover a malodour thereof. They are generally in the form of perfume concentrates, perfumes, eaux de parfum, eaux de toilette, or colognes and body splashes.

The words "perfume" and "fragrance" are used here interchangeably to designate the component in the composition that is formed of perfuming ingredients, i.e. ingredients capable of imparting or modifying the odour of skin or hair.

By a "perfuming ingredient" it is meant here a compound of current use in perfumery, which is used essentially for its ability to smell pleasantly and to be capable of imparting a pleasant odour to the products into which it is incorporated, or to the surfaces, such as skin or hair, to which it is applied, on its own or in admixture with other such ingredients. In other words, a perfuming ingredient has the ability to impart or modify, in a positive or pleasant way, the odour of a composition or surface. When the latter has a malodour, the perfuming ingredient may also be capable of covering such malodour so as to render the overall perceived odour pleasant.

By "modulator" it is understood here an agent having the capacity to affect the manner in which the odour, in particular its evaporation rate and intensity, of the compositions incorporating said modulator can be perceived by an observer or user thereof, over time, as compared to the same perception in the absence of the modulator. In particular, according to the invention, PPG-3 myristyl ether is a modulator of the perceived tenacity of the compositions according to the invention, i.e. it is used to prolong the time during which their fragrance is perceived to have an acceptable intensity, as compared to the perception when PPG-3 myristyl ether is not used in the composition.

A "fragrance modulator formed of PPG-3 myristyl ether" means here a fragrance modulator based on PPG-3 myristyl ether, but which may also contain another substance or substances having a similar modulator effect on the evaporation of the fragrance, under the same conditions. The fragrance modulator, as defined here, consists of substances capable of increasing the tenacity of the fragrance component, and therefore of the composition, as compared to its tenacity in the absence of fragrance modulator, and contains at least 30% of PPG-3 myristyl ether and, more preferably, a predominant amount (more than 50% by weight of the total weight of fragrance modulator) of PPG-3 myristyl ether.

The perception or impact of a perfuming ingredient, or of a mixture of perfuming ingredients forming the fragrance component, is understood here to be prolonged or delayed in the presence of the modulator, i.e. its top and heart notes become "tenacious", meaning that they can be perceived by the user and any other individuals in the surroundings for a longer time than if the fragrance had been applied on its own, in the absence of the modulator, to skin or hair.

The definitions here above apply to any and all embodiments of the invention here-described and in particular to any and all embodiments of the compositions according to the invention.

The perfume or fragrance component present in the composition of the invention is defined here as a compound which is used to impart a hedonic effect. In other words such a perfuming component, in order to be considered as such, must be recognized by a person skilled in the art as being able to impart or modify in a positive, desirable or pleasant way the odour of the composition, article or surface on which it is applied, and not just as having an odour. Compounds capable of modifying the perception by a consumer of a compound as defined above are also considered as the fragrance component in the composition of the invention.

Typically, the fragrance component of the composition is a mixture of perfuming ingredients, possibly together with current perfume carriers.

By "perfumery carrier" we mean here a material which is practically neutral from a perfumery point of view, i.e. which does not significantly alter the organoleptic properties of perfuming components. Said carrier may preferably be a liquid and will typically be a solvent such as dipropyleneglycol, diethyl phthalate, isopropyl myristate, benzyl benzoate, 2-(2-ethoxyethoxy)-1-ethanol or ethyl citrate (triethyl citrate) are the most commonly used.

According to a particular embodiment of the invention, the composition comprises a fragrance component wherein 50% to 70%, or even more, of its weight is formed of perfuming ingredients having a calculated vapor pressure V comprised in the range $0.05<V<300$ Pa.

Also, the use of PPG-3 myristyl ether as a modulator of the composition's tenacity has proved to be even more advantageous when the fragrance component comprises the above-mentioned amounts of particularly volatile ingredients, i.e. ingredients having a vapor pressure between $0.2<V<200$ Pa, the resulting compositions of the invention being preferred.

The nature and type of the perfuming ingredients in the fragrance component of the compositions according to the invention can be selected by the skilled person, on the basis of its general knowledge together with the teachings contained herein, and according to the intended use or application and the desired perfuming effect. In general terms, these perfuming ingredients belong to chemical classes as varied as alcohols, aldehydes, ketones, esters, ethers, acetates, nitriles, terpene hydrocarbons, nitrogenous or sulfurous heterocyclic compounds and essential oils, and can be of natural or synthetic origin. Many of these ingredients are in any case listed in reference texts such as the book by S. Arctander, Perfume and Flavor Chemicals, 1969, Montclair, N.J., USA, or its more recent versions, and in other works and textbooks of a similar nature, as well as in the abundant patent literature in the field of perfumery.

It is also understood that said perfuming ingredients can be admixed with compounds known to release in a controlled manner various types of perfuming ingredients, either through chemical reaction cleavage of chemical bonds of heavier precursors, or through physical release of such perfuming compounds, for example when the latter are encapsulated or carried in an emulsion, microemulsion and/or nanoemulsion type perfume carrier system. Such chemical release molecules are generally designated as "release systems" and they are commonly used in fragrances to prolong the release in time of specific odorants and their olfactive impact over time, as compared to the olfactive effect that each such odorant could produce when used as such and not in the form of an heavier precursor thereof.

Provided that the fragrance component comprises at least 40% of its weight, and more preferably at least 50%, and typically 50 to 70% or more, by weight of perfuming ingredients having a vapor pressure as defined above, the remainder of the fragrance component may be formed of any common or current perfuming ingredient or ingredients, used as single chemical entities, as mixtures of isomers or with other perfuming ingredients, or in the form of perfumery release systems as cited above. Examples of such release systems are found for example in WO 95/04809, EP 0971021, WO 03/049666, EP 0936211, WO 99/60990, WO 01/28980, WO 08/093272, WO 98/47477, US 2004/0102357, DE 30 03 494 and WO 95/08976, to name but a few documents where such systems are described in detail.

Preferred perfuming ingredients having the desired calculated vapor pressure (calculated according to the reference program EPI suite v4.00, 2000-2008 U.S. Environmental Protection Agency) to form the at least 40% by weight of the fragrance component, are cited in Table 1 hereafter.

TABLE 1

Perfuming ingredients for use in the invention

| Ingredients | Calculated Vapor Pressure (Pa) |
|---|---|
| Limonene | 193.285 |
| Hexyl Acetate | 193.285 |
| Cis-3-Hexenyl Acetate* | 151.962 |
| Cis-3-Hexenol* | 124.902 |
| Ethyl Acetoacetate | 123.836 |
| Rose Oxide | 87.578 |
| 3-Methyl-2-Hexenyl Acetate* | 73.182 |
| 2,4-Dimethyl-3-cyclohexene-1-carbaldehyde* | 46.922 |
| Benzyl Acetate | 24.927 |
| Linalyl Acetate | 17.462 |
| Dihydromyrcenol | 16.529 |
| Styrallyl Acetate | 14.930 |
| Citral | 12.170 |
| Linalol | 11.091 |
| (+−)-3-Methoxy-7,7-Dimethyl-10-Methylene-Bicyclo[4.3.1]Decane* | 4.199 |
| Geranyl Acetate | 3.839 |
| Phenethylol | 3.239 |
| Allyl Cycloheylpropanoate | 2.906 |
| Methyl Anthranilate | 2.626 |
| alpha-Damascone* | 2.479 |
| Ethyl Linalol | 2.359 |
| Ethyl (2E,4Z)-2,4-Decadienoate* | 2.306 |
| Citronellol | 2.253 |
| Geraniol | 2.119 |
| Myrrhone ®[1]* | 1.946 |
| Ethyl (2E)-2,4,7-Decatrienoate* | 1.746 |
| Diethyl 1,4-cyclohexane dicarboxylate* | 1.680 |
| Indol | 1.613 |
| Florol ®[2]* | 1.600 |
| 4-Nonanolide* | 1.573 |
| Heliotropine | 1.413 |
| 4-Cyclohexyl-2-methyl-2-butanol* | 1.333 |
| Eugenol | 1.264 |
| Cyclosal | 1.141 |
| Hivernal ®[8]* | 0.873 |
| 4-Methyl-3-decen-5-ol | 0.793 |

TABLE 1-continued

Perfuming ingredients for use in the invention

| Ingredients | Calculated Vapor Pressure (Pa) |
|---|---|
| gamma-n-Decalactone | 0.682 |
| Florazolone ™[9] | 0.665 |
| Bourgeonal ®[3] | 0.665 |
| gamma-Undecalactone* | 0.545 |
| Cashmeran | 0.537 |
| Lilial ®[4] | 0.477 |
| Romandolide ®[5]* | 0.357 |
| (Methoxymethoxy)Cyclododecane | 0.312 |
| 2,2,7/8,9/10-Tetramethylspiro[5.5]undec-8-en-1-one* | 0.152 |
| Iso E Super[6] | 0.147 |
| Calone ®[10]* | 0.097 |
| Coumarine | 0.088 |
| Sandalore ®[7] | 0.059 |
| Hedione ®* | 0.055 |
| Heliopropanal | 0.055 |

*origin: Firmenich SA, Geneva Switzerland
[1]4-(2,2,e-3,t-6-tetramethyl-R-1-cyclohexyl)-3-buten-2-one
[2]tetrahydro-2-isobutyl-4-methyl-4(2H)-pyranol
[3]3-(4-tert-butylphenyl)propanal; origin: Givaudan SA, Vernier, Switzerland
[4]3-(4-tert-butylphenyl)-2-methylpropanal; origin: Givaudan SA, Vernier, Switzerland
[5](1S,1'R)-[1-(3',3'-Dimethyl-1'-cyclohexyl)ethoxycarbonyl]methyl propanoate
[6]origin: International Flavors & Fragrances, USA
[7]3-methyl-5-(2,2,3-trimethyl-3-cyclopenten-1-yl)-2-pentanol; origin: Givaudan SA, Vernier, Switzerland
[8]3-(3,3/1,1-dimethyl-5-indanyl)propanal
[9]3-(4/2-Ethylphenyl)-2,2-dimethylpropanal; origin: Givaudan SA, Vernier, Switzerland
[10]7-Methyl-2H,4H-1,5-benzodioxepin-3-one Amongst all the compositions of the invention, those wherein said fragrance component contains at least 40%, and more preferably at least 50%, by weight of perfuming ingredients selected in the group consisting of the ingredients mentioned in the said Table are preferred.

As indicated above, the fragrance component forms 3 to 40% by weight of the weight of the composition. More particular embodiments of the invention's composition will comprise 3 to 25%, and more specifically 5 to 20%, by weight of fragrance component, relative to the total weight of the composition.

Therefore, amongst the compositions according to the invention which are of a more specific nature one can cite compositions which comprise 3 to 25%, or 5 to 20%, by weight of fragrance component, at least 40% by weight of which, and more preferably 50 to 70% by weight of which, is formed of ingredients having a calculated vapor pressure V comprised in the range $0.05 < V < 300$ Pa, and more preferably a calculated vapour pressure V of $0.2 < V < 200$ Pa.

Component c) of the any embodiment of the invention's compositions is a fragrance modulator as defined earlier in this description, present in an amount of between 0.01 and 20% by weight of the composition's weight and, in more particular embodiments, between 0.5 and 10% by weight. More preferred amounts of fragrance modulator in any such composition vary from 0.5 to 6%, or even between 1 and 5%, by weight of the total weight of the composition. Preferably, at least 50 by weight of the fragrance modulator's weight is PPG-3 myristyl ether, the remainder to 100% possibly being one or more other modulators or co-modulators. PPG-3 Myristyl ether is commercialized by Evonik-Goldschmidt for example, under the tradename Tegosoft™ APM or yet by Degussa under the tradename Varonic® APM. There are however other suppliers of this material, which is also sold under other commercial designations. Any such commercial forms of PPG-3 myristyl ether are appropriate for use as component c) of the invention's compositions.

Therefore, the invention relates to compositions as defined above which contain PPG-3 myristyl ether, or a mixture of PPG-3 myristyl ether with other modulators, namely CERAPHYL® ICA and/or Schercemol™ NGDO ester, as the fragrance modulator.

Preferred co-modulators according to the present invention are the compounds known commercially as CERAPHYL® ICA (isocetyl alcohol; available from International Specialty Products) and Schercemol™ NGDO ester (Neopentyl glycol diethylhexanoate; available from Lubrizol Advanced Materials, USA), or any other commercial designations thereof, since the same materials may be sold by other suppliers under other tradenames. The fragrance modulator of any composition according to the invention may therefore be composed of PPG-3 myristyl ether, or be a mixture of the latter with one or both of these two co-modulators, wherein PPG-3 myristyl ether forms 50% by weight or more of the weight of the fragrance modulator mixture. In this context, it was possible to establish that the compositions according to the invention which contained a fragrance modulator formed of PPG-3 myristyl ether together with CERAPHYL® ICA and/or Schercemol™ NGDO ester, wherein the weight concentration of PPG-3 myristyl ether was 50 weight % of the combined weight of the modulator mixture and the other fragrance modulator or modulators formed the remainder 50% weight of component b) in the compositions according to the invention gave much appreciated results.

The fragrance modulator mixtures of PPG-3 myristyl ether together with CERAPHYL® ICA and Schercemol™ NGDO ester, wherein the weight concentration of PPG-3 myristyl ether was 50% of the combined weight of the mixture and the other two components thereof were present in equal weight % amounts in the mixture, also improved advantageously the intensity of the fragrance perceived over time. In particular, mixtures of PPG-3 myristyl ether with CERAPHYL® ICA, in a 1:1 weight ratio, gave optimal fragrance release results after 4 and 8 h of application of the composition on the skin.

Therefore, all the compositions according to the invention that contained mixtures of at least 50% weight of PPG-3 myristyl ether, together with CERAPHYL® ICA and/or Schercemol™ NGDO ester proved to be prime compositions for the objective of the invention, i.e. to prolong the perception of the fragrance from the surface on which it had been applied, as compared to the use of the fragrance without any modulator, or even when only PPG-3 myristyl ether was used as the modulator.

Ethanol may be present in any of the compositions in a concentration of 40 to 90% w/w, and more specifically it will form from 50 to 80%, or even from 60 to 85%, by weight of the total weight of the composition. Any acceptable quality of ethanol, compatible with the requirements for use in topical applications, is convenient for use in the compositions according to the invention.

The amount of water present in any embodiment of the invention's compositions shall not be above 20% by weight, and more preferably it shall be 10% or less by weight, relative to the weight of the composition. This amount may be result from the amount of water present in the ethanol used in the composition, or not, as the case may be.

It goes without saying that the invention encompasses any composition comprising the components a) to c), or a) to d), cited before in this text, in any embodiment wherein each such ingredient is present in any appropriate amount thererelative defined in this text, independently of the amount of any one of the three other ingredients. Many such compositions can therefore be encompassed, wherein one or more such ingredients are combined in broader or more specific concentration ranges.

It has been ascertained that, amongst such compositions, those consisting of:
a) a fragrance component, in an amount of between 5 and 20% by weight of the composition's weight, at least 50% by weight of the total weight of which is formed of perfuming ingredients having a calculated vapor pressure V comprised in the range $0.05 < V < 300$ Pa;
b) from 60 to 85% by weight, relative to the total weight of the composition, of ethanol;
c) from 0.5 to 6% by weight, relative to the total weight of the composition, of PPG-3 myristyl ether; and
d) from 0 to 10% by weight of water, relative to weight of the composition, are specific formulations according to the invention, wherein best results, as regards tenacity performance improvement, were observed.

According to other preferred embodiments, there are provided compositions consisting of:
a) a fragrance component, in an amount of between 5 and 10% by weight of the composition's weight, at least 50% by weight of the total weight of which is formed of perfuming ingredients having a calculated vapor pressure V comprised in the range $0.05 < V < 300$ Pa;
b) from 70 to 85% by weight, relative to the total weight of the composition, of ethanol;
c) from 2 to 6% by weight, relative to the total weight of the composition, of PPG-3 myristyl ether; and
d) from 0 to 5% by weight of water, relative to weight of the composition.

All compositions of the invention defined in the present disclosure are capable of efficiently prolonging the perception of the fragrance component when compared to similar compositions differing only in that the fragrance modulator is absent and has been replaced by ethanol or water. In addition, it has been established that the PPG-3 myristyl ether based fragrance modulators according to the invention do not affect negatively the olfactive quality and stability of the fragrance, even when the compositions have been submitted to a long storage period of time, i.e. for 2 months at 45° C., unlike what can be observed when some conventional fixatives are employed.

A composition according to any of the embodiments described above is a useful perfuming material, which can be advantageously used in fine perfumery for products intended to perfume skin and hair. Indeed, such compositions may be advantageously employed to achieve a more controlled deposition, and consequent release, of the perfume.

Another object of the present invention relates to a method for perfuming skin or hair, or to a method for intensifying or prolonging the diffusion effect of the characteristic fragrance of a fragrance component on skin or hair, characterized in that a body surface is treated with any one composition as defined in this description, under conditions which are susceptible of allowing the release of said fragrance component, in a better performing manner than with prior known perfumes, wherein the fragrance modulator is absent.

The compositions according to the invention can be prepared by simple admixture of their components in a generally known manner.

EXAMPLES

The invention will now be described in further detail by way of the following examples, wherein the abbreviations have the usual meaning in the art. In all the evaluation tests described below, involving the use of panelists, the evaluation was carried out in a blind test, meaning that the panelists did not know the composition of the evaluated sample.

Examples 1 to 3

Compositions According to the Invention and Use Thereof

A perfume, intended to form the fragrance component of the compositions of the invention, was prepared by admixing the following ingredients, in the amounts indicated in the Table 2 below.

TABLE 2

Fragrance I

| Ingredients | Parts (by weight) |
|---|---|
| (Z)-3-Hexen-1-ol | 6.00 |
| Ethyl acetoacetate | 7.80 |
| Ethyl 2-methyl-pentanoate[1] | 8.64 |
| (Z)-3-Hexen-1-yl Acetate | 8.52 |
| Limonene | 8.16 |
| Dihydromyrcenol[2] | 9.36 |
| Zestover[3] | 8.28 |
| Rose oxide | 9.24 |
| Benzyl acetate | 9.00 |
| Ethyl linalool | 20.16 |
| Citral | 18.24 |
| Indole | 7.02 |
| Heliotropine | 9.00 |
| Methyl anthranilate | 9.06 |
| Eugenol | 9.84 |

TABLE 2-continued

Fragrance I

| Ingredients | Parts (by weight) |
|---|---|
| α-Damascone | 11.52 |
| Coumarine | 8.76 |
| Allyl cyclohexyl propionate | 11.76 |
| Ethyl (2E,4Z)-2,4-decadienoate | 11.76 |
| Lilial ®[4] | 12.24 |
| Total | 204.36 |

[1] Origin: Firmenich SA, Geneva, Switzerland
[2] Origin: International Flavors & Fragrances, USA
[3] 2,4-dimethyl-3-cyclohexene-1-carbaldehyde; origin: Firmenich SA, Geneva, Switzerland
[4] 3-(4-tert-butylphenyl)-2-methylpropanal, origin: Givaudan SA, Vernier, Switzerland With Fragrance I, there were prepared three compositions according to the invention, by admixture of the components described in Table 3, in the proportions indicated.

TABLE 3

Compositions according to the invention

| | Composition (weight %) | | |
|---|---|---|---|
| Component | A | B | C |
| Fragrance I | 10.00 | 10.00 | 10.00 |
| Ethanol 96% | 79.42 | 79.42 | 79.42 |
| Tegosoft ™ APM | 5.00 | 3.00 | 1.00 |
| Demineralised water | 5.58 | 7.58 | 9.58 |

In parallel, a blank composition was prepared by replacing the fragrance modulator Tegosoft™ APM, in the amount indicated in the table for Composition A, B, respectively C, by the same amount of demineralised water.

Each of compositions A, B, C was then evaluated on a blind test against the blank, by a panel of 30 individuals. The latter were asked to evaluate the odour intensity perceived, on a scale of 1 to 10, from each pair of samples, i.e. that of the composition according to the invention and the blank. On the scale 1 to 10, 0 represented an inability to detect the odour and 10 represented a very strong odour.

The samples were evaluated after application on glass slides, the latter having been placed on a hot plate at a constant temperature of 32° C., for the desired amount of time. The results of the blind tests thus carried out were averaged and treated for variance following Duncan's post-hoc analysis ($\alpha=0.05$).

Figure 1:
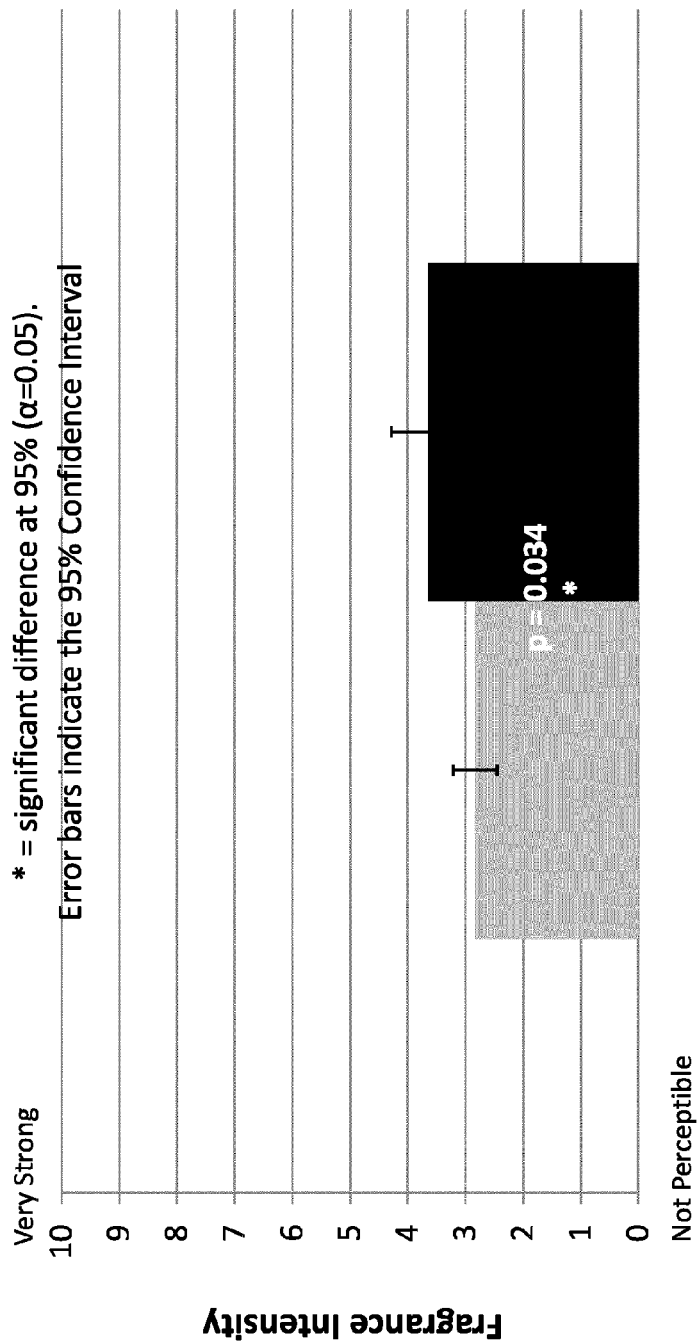
FIG. 1: This figure shows the odour intensity of Composition A of the invention, as compared to a blank comprising no fragrance modulator, about 8 hours after application thereof.

FIG. 1 represents the results of a blind test evaluation, after about 8 h at 32° C., of Composition A against the blank. It is clearly seen from this figure that the fragrance modulator Tegosoft™ APM, at a concentration of 5% by weight, strongly enhances the fragrance intensity perception by the user, after 8 h of application of Composition A on the plate.

Figure 2:
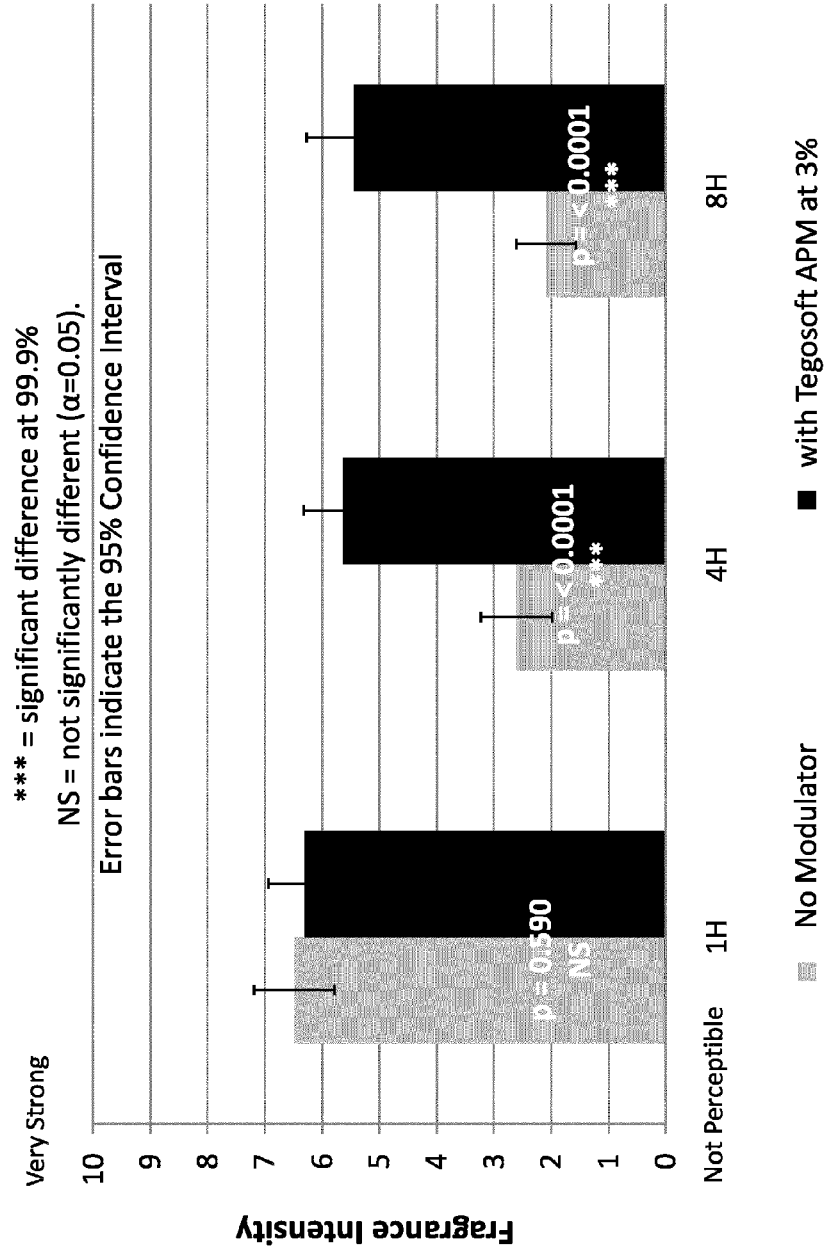
FIG. 2: This figure shows the odour intensity of Composition B of the invention as compared to a blank comprising no fragrance modulator and as a function of time elapsed since composition application.
Figure 3:
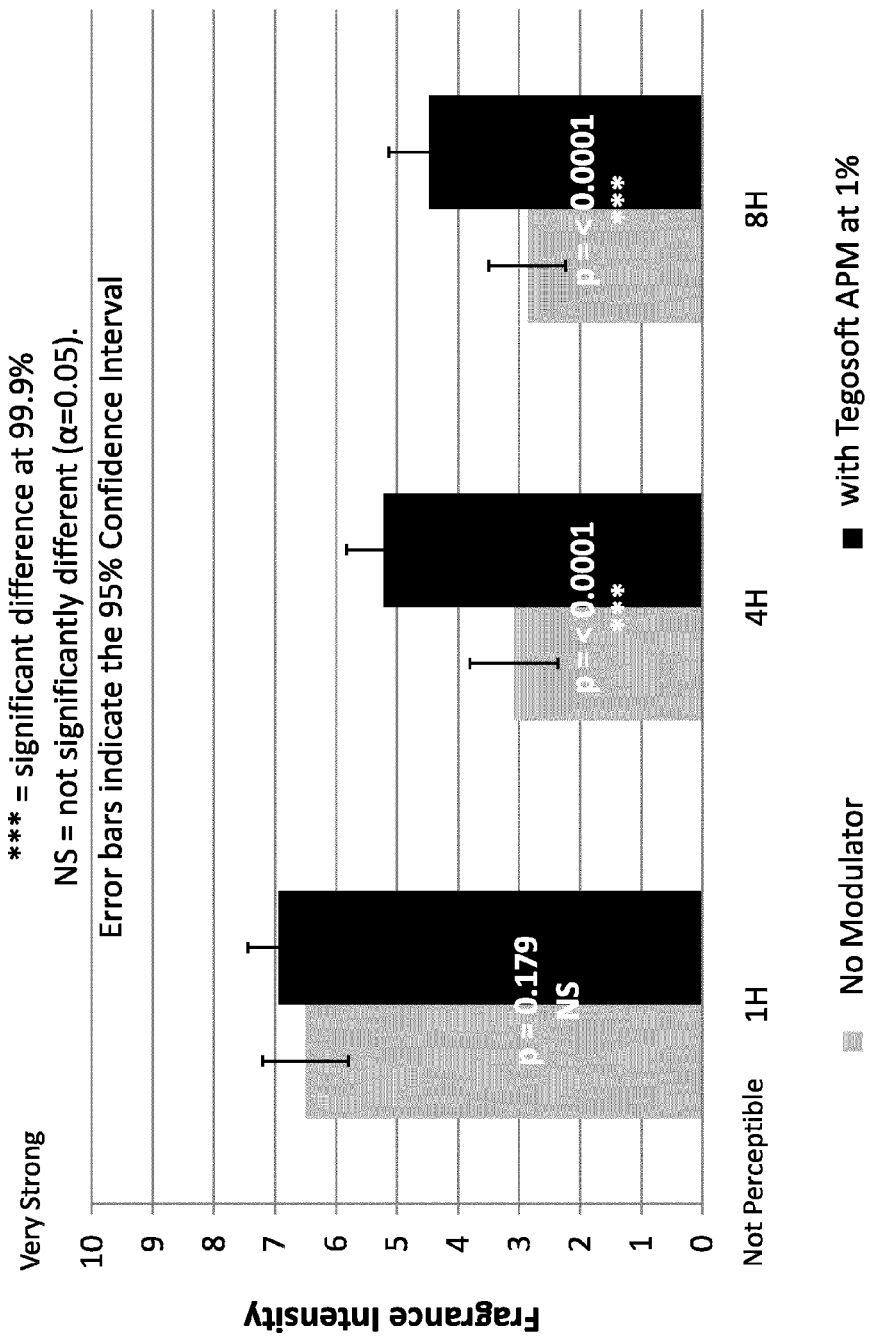
FIG. 3: This figure shows the odour intensity of Composition C of the invention as compared to a blank comprising no fragrance modulator and as a function of time elapsed since composition application.

FIGS. 2 and 3 show the effect over time of the same fragrance modulator, when used at lower concentrations (Compositions B and C). The effect of Tegosoft™ APM is particularly marked after 4 and 8 hours of application of the two cited compositions according to the invention on the carrier plate.

Example 4

Composition According to the Invention and Use Thereof

A perfume, intended to form the fragrance component of compositions of the invention, was prepared by admixing the following ingredients, in the amounts indicated in the Table 4 below.

TABLE 4

Fragrance II

| Ingredients | Parts (by weight) |
|---|---|
| Cis-3-Hexenyl Acetate | 2 |
| Styrallyl Acetate | 1 |
| Ethyl Acetoacetate | 5 |
| Allyl Cyclohexylpropionate | 1 |
| Damascone Alpha | 2 |
| Dihydromyrcenol | 14 |
| Ethyl Linalol | 34 |
| Geraniol | 10 |
| Iso E Super | 10 |
| Lilial ® | 100 |
| Limonene Dist | 105 |
| Florol ® | 110 |
| Rose Oxide | 5 |
| Phenylethyl Alcohol | 85 |
| Cis-3-Hexenol | 1 |
| Zestover | 10 |
| Total | 495 |

With Fragrance II, there was prepared a composition according to the invention, by admixture of the components described in Table 5, in the proportions indicated.

TABLE 5

Composition D according to the invention

| Component | Composition (weight %) |
|---|---|
| Fragrance II | 10.00 |
| Ethanol 96% | 79.42 |
| Tegosoft ™ APM | 3.00 |
| Demineralised water | 7.58 |

In parallel, a blank composition was prepared by replacing the fragrance modulator Tegosoft™ APM, in the amount indicated in the table for Composition D, by the same amount of demineralised water.

Composition D was then evaluated on a blind test against the blank, by a panel of 5 experts in odour evaluation. The latter were asked to evaluate the odour intensity perceived, on a scale of 1 to 10, from the pair of samples, i.e. that of the composition according to the invention and the blank. On the scale 1 to 10, 0 represented an inability to detect the odour and 10 represented a very strong odour.

The samples were evaluated after application on glass slides, the latter having been placed on a hot plate at a constant temperature of 32° C., for the desired amount of time. The results of the blind tests thus carried out were averaged.

Figure 4:
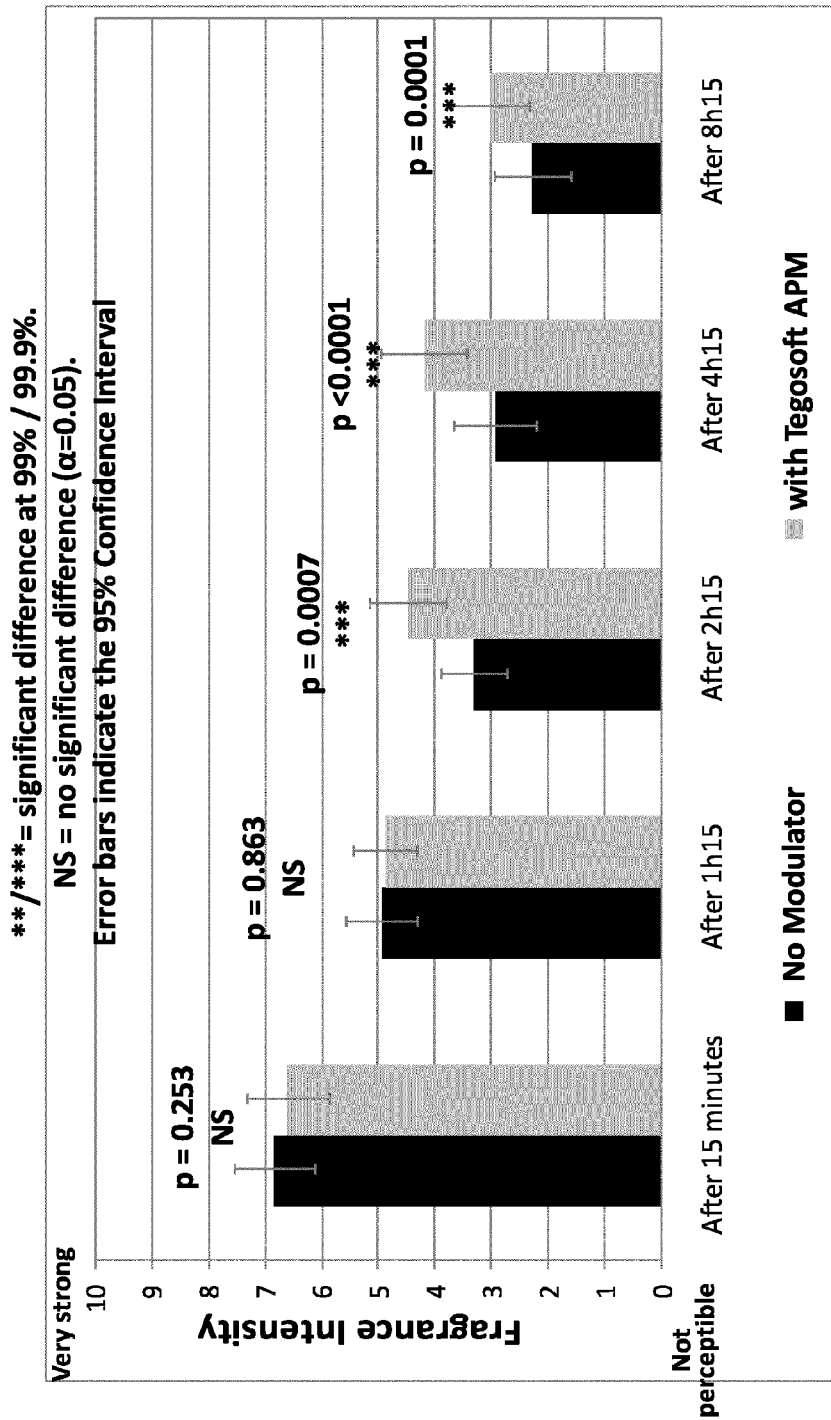
FIG. 4: This figure shows the odour intensity of Composition D of the invention as compared to a blank comprising no fragrance modulator, over time, after application thereof.

FIG. 4 shows the effect over time of the fragrance modulator, when used at the concentration indicated in Table 5. The effect of Tegosoft™ APM is marked at 2 hours, 4 hours and 8 hours after composition application according to the invention on the carrier plate.

Examples 5 to 12

Compositions According to the Invention and Use Thereof

A perfume, intended to form the fragrance component of compositions of the invention, was prepared by admixing the following ingredients, in the amounts indicated in the Table 2 above.

With Fragrance I as described in Table 2, there were prepared eight compositions according to the invention, by admixture of the components described in Table 6 below, in the proportions indicated.

TABLE 6

Compositions A and E to L

| Component | Composition (weight %) | | | | | | | | |
|---|---|---|---|---|---|---|---|---|---|
| | A | E | F | G | H | I | J | K | L |
| Fragrance I | 10.00 | 10.00 | 10.00 | 10.00 | 10.00 | 10.00 | 10.00 | 10.00 | 10.00 |
| Ethanol 96% | 79.42 | 79.42 | 79.42 | 79.42 | 79.42 | 79.42 | 79.42 | 79.42 | 79.42 |
| Tegosoft ™ APM | 5.0 | 3.5 | 3.5 | 4.5 | 4.5 | 2.5 | 1.66 | 2.5 | 2.5 |
| Ceraphyl ® ICA | | 1.5 | | 0.5 | | 1.25 | 1.66 | 2.5 | |
| Schercemol ™ NGDO | | | 1.5 | | 0.5 | 1.25 | 1.66 | | 2.5 |
| Demineralised water | 5.58 | 5.58 | 5.58 | 5.58 | 5.58 | 5.58 | 5.58 | 5.58 | 5.58 |

In parallel, a blank composition was prepared by replacing the fragrance modulator Tegosoft™ APM in the amount indicated in the table for Composition A, by the same amount of demineralised water.

Each composition A and E to L was then evaluated on a blind test against the blank, by a panel of 30 individuals. The latter were asked to evaluate the odour intensity perceived, on a scale of 1 to 10, from the successive pairs of samples, i.e. that of each of the compositions according to the invention against the blank. On the scale 1 to 10, 0 represented an inability to detect the odour and 10 represented perception of a very strong odour.

The samples were evaluated after application on glass slides, the latter having been placed on a hot plate at a constant temperature of 32° C., for the desired amount of time. The results of the blind tests thus carried out were averaged and treated for variance following Duncan's post-hoc analysis ($\alpha=0.05$).

Figure 5:
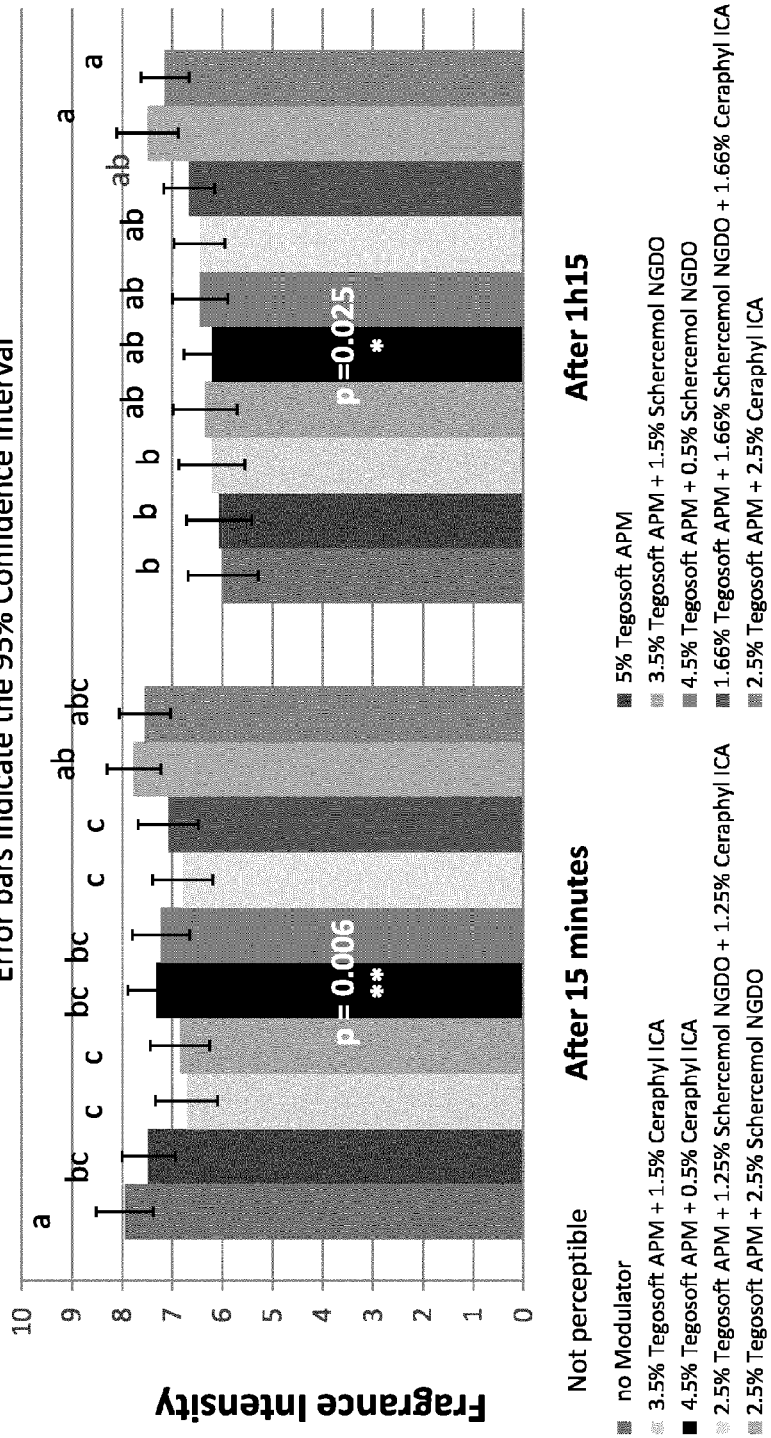
FIG. 5: This figure shows the odour intensity of compositions E to L according to the invention, containing Fragrance I combined with mixtures of Tegosoft™ APM with Schercemol™ NGDO ester and/or Ceraphyl® ICA, in a variety of relative concentrations, as compared to the odour intensity of the Composition A which contains the same fragrance combined with Tegosoft™ APM alone as the modulator, at two points in time after composition application.
Figure 6:
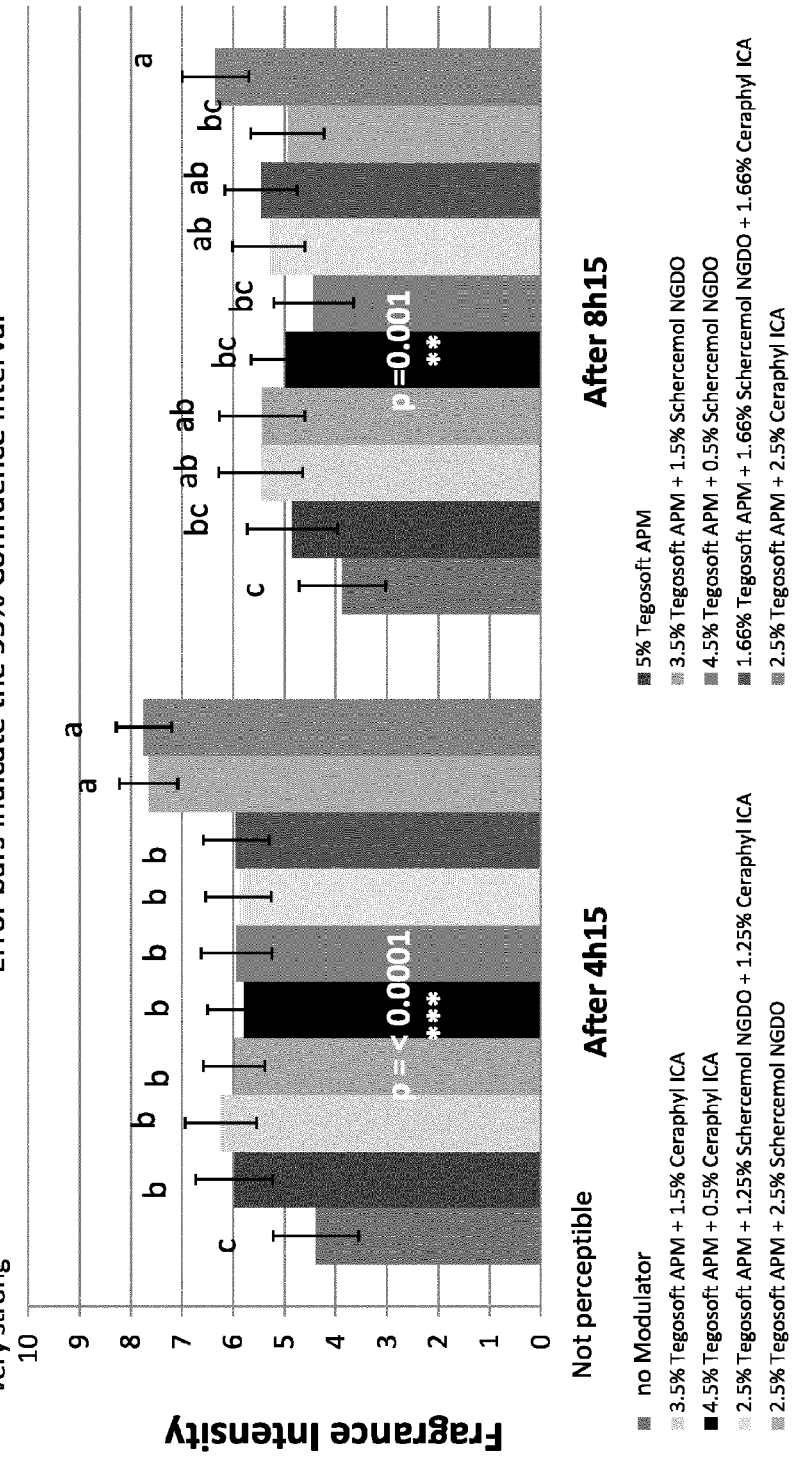
FIG. 6: This figure shows the odour intensity of Fragrance I when combined with a variety of fragrance modulators consisting of mixtures of Tegosoft™ APM with Schercemol™ NGDO ester and/or Ceraphyl® ICA, as compared to the odour intensity of the same fragrance when combined with Tegosoft™ APM alone, at two points in time after composition application.

FIGS. 5 and 6 show the results of the blind test evaluation of the effect over time of compositions A and E-L, when used at the concentrations indicated in Table 6, compared to the blank fragrance sample without fragrance modulator.

FIG. 5 shows that, after a short period of 15 minutes, all compositions A and E-L are very intense; after 1.25 hours all compositions are also intense, however the compositions containing a 1:1 mixture of Tegosoft™ APM and Ceraphyl® ICA (composition K) or a 1:1 mixture of Tegosoft™ APM and Schercemol™ NGDO (composition L) are perceived by the panel as developing a significantly more intense odor than the blank or indeed than the composition containing Tegosoft™ APM alone (composition A).

FIG. 6 shows the odor intensity at longer times after application of the compositions in Table 6. After around 4 hours, all compositions containing mixtures of fragrance modulators have odors that are significantly stronger than that of the blank, but in particular compositions containing a 1:1 mixture of Tegosoft™ APM and Ceraphyl® ICA (composition K) or a 1:1 mixture of Tegosoft™ APM and Scheremol™ NGDO (composition L) stand out in that they are perceived by the panel as quite significantly more intense than the blank or than any other composition.

After about 8 hours, while compositions E, F, I and J are perceived as significantly more intense than the blank, the 1:1 mixture of Tegosoft™ APM and Ceraphyl® ICA (composition K) is perceived as being significantly much more intense than the blank.

What is claimed is:

1. A composition consisting of:
    a) a fragrance component, in an amount of between 3 and 40% by weight of the composition's weight, at least 40% by weight of the total weight of said fragrance component being formed of perfuming ingredients having a calculated vapor pressure V comprised in the range 0.05<V<300 Pa;
    b) from 40 to 90% by weight, relative to the total weight of the composition, of ethanol;
    c) from 0.01 to 20% by weight, relative to the total weight of the composition, of a fragrance modulator comprising PPG-3 myristyl ether, provided that said fragrance modulator comprises less than 50% by weight of isocetyl alcohol and less than 50% by weight of neopentyl glycol diethylhexanoate; and
    d) optionally water; and
    wherein the sum of the weights of ingredients a) to d) in the composition adds up to at least 98%) of the composition's weight.

2. A composition according to claim 1 wherein said perfuming ingredients forming at least 40% by weight of the fragrance component are selected from the group consisting of limonene, hexyl acetate, cis-3-hexenyl acetate, cis-3-hexenol, ethyl acetoacetate, rose oxide, 3-methyl-2-hexenyl acetate, 2,4-dimethyl-3-cyclohexene-1-carbaldehyde, benzyl acetate, linalyl acetate, dihydromyrcenol, styrallyl acetate, citral, linalol, (+)-3-methoxy-7,7-dimethyl-10-methylene, bicyclo[4.3.1]decane, geranyl acetate, phenethylol, allyl cycloheylpropanoate, methyl anthranilate, alpha-damascone, ethyl linalol, ethyl (2e,4z)-2,4-decadienoate, citronellol, geraniol, 4-(2,2,c-3,t-6-tetramethyl-r-1-cyclohexyl)-3-buten-2-one, ethyl (2e)-2,4,7-decatrienoate, diethyl 1,4-cyclohexane dicarboxylate, indol, tetrahydro-2-isobutyl-4-methyl-4(2h)-pyranol, 4-nonanolide, heliotropine, 4-cyclohexyl-2-methyl-2-butanol, eugenol, cyclosal, 3-(3,3/1,1-dimethyl-5-indanyl)propanal, 4-methyl-3-decen-5-ol, gamma-n-decalactone, 3-(4/2-ethylphenyl)-2,2-dimethylpropanal, 3-(4-tert-butylphenyl)propanal, gamma-undecalactone, cashmeran, 3-(4-tert-butylphenyl)-2-methylpropanal, (1s,1'r)-[1-(3',3'-dimethyl-1'-cyclohexyl) ethoxycarbonyl]methyl propanoate, (methoxymethoxy) cyclododecane, 2,2,7/8,9/10-tetramethylspiro[5.5]undec-8-en-1-one, 1-(1,2,3,4,5,6,7,8-octahydro-2,3,8,8,-tetramethyl-2-naphthyl)ethan-1-one, 7-methyl-2h,4h-1,5-benzodioxepin-3-one, coumarine, 3-methyl-5-(2,2,3-trimethyl-3-cyclopenten-1-yl)-2-pentanol, methyl dihydrojasmonate, and heliopropanal.

3. A composition according to claim 2, wherein the fragrance modulator comprising PPG-3 myristyl ether is present in an amount of between 0.05 and 10% weight, relative to the total weight of composition.

4. A composition according to claim 2, wherein said perfuming ingredients form at least 50% by weight of the fragrance component.

5. A composition according to claim 1, wherein said composition contains up to 20% by weight of water.

6. A composition according to claim 5, wherein the fragrance modulator further comprises a co-modulator selected from the group consisting of isocetyl alcohol, neopentyl glycol diethylhexanoate and their mixtures.

7. A composition according to claim 1, wherein the fragrance modulator comprises at least 50% by weight, relative to the total weight of fragrance modulator, of PPG-3 myristyl ether.

8. A composition according to claim 1, wherein said composition contains a fragrance modulator comprising PPG-3 myristyl ether together with isocetyl alcohol and/or neopentyl glycol diethylhexanoate, wherein the weight concentration of PPG-3 myristyl ether is 50% of the combined weight of the modulator mixture and the other fragrance modulators form the remainder 50% weight of the modulator mixture.

9. A composition according to claim 1, wherein said composition consists of:
    a) a fragrance component, in an amount of between 5 and 20% by weight of the composition's weight, at least 50% by weight of the total weight of which is formed of perfuming ingredients having a calculated vapor pressure V comprised in the range 0.05<V<300 Pa;
    b) from 60 to 85% by weight, relative to the total weight of the composition, of ethanol;
    c) from 0.5 to 6% by weight, relative to the total weight of the composition, of PPG-3 myristyl ether or a mixture thereof with isocetyl alcohol and/or neopentyl glycol diethylhexanoate; and
    d) from 0 to 10% by weight of water, relative to the total weight of the composition.

10. A composition according to claim 1, wherein said composition consists of:
    a) a fragrance component, in an amount of between 5 and 10% by weight of the composition's weight, at least 50% by weight of the total weight of which is formed of perfuming ingredients having a calculated vapor pressure V comprised in the range 0.05<V<300 Pa;
    b) from 70 to 85% by weight, relative to the total weight of the composition, of ethanol;
    c) from 2 to 6% by weight, relative to the total weight of the composition, of PPG-3 myristyl ether or a mixture thereof with isocetyl alcohol and/or neopentyl glycol diethylhexanoate; and
    d) from 0 to 5% by weight of water, relative to the total weight of the composition.

11. A composition according to claim 1 in the form of a perfume, an eau de toilette, an eau de parfum, a cologne or a body splash or spray.

12. A method to confer, enhance, improve or modify the odour properties of a body surface, comprising contacting or treating said body surface with a composition as defined in claim 1 in a generally known manner.

13. A method for modulating the perceived olfactive impact of a composition, which method comprises adding a modulating agent formed of PPG-3 myristyl ether to a fragrance component as defined in claim 1 in the relative proportions indicated, and completing the composition with ethanol and optionally water.

14. A method for increasing the long-lastingness of a fragrance component in an ethanol based composition, comprising preparing a composition as defined in claim 1 using said fragrance component together with a fragrance modulator formed of PPG-3 myristyl ether, in the relative proportions defined in claim 1.

15. A composition according to claim 1, wherein the fragrance modulator comprising PPG-3 myristyl ether is present in an amount of between 0.5 and 6% by weight, relative to the total weight of composition.

16. A composition comprising:
a) a fragrance component, in an amount of between 3 and 40% by weight of the composition's weight, at least 40% by weight of the total weight of said fragrance component being formed of perfuming ingredients having a calculated vapor pressure V comprised in the range $0.05<V<300$ Pa;
b) from 40 to 90% by weight, relative to the total weight of the composition, of ethanol;
c) from 0.01 to 20% by weight, relative to the total weight of the composition, of a fragrance modulator comprising PPG-3 myristyl ether, provided that said fragrance modulator comprises less than 50% by weight of isocetyl alcohol and less than 50% by weight of neopentyl glycol diethylhexanoate; and
d) optionally water;
wherein the sum of the weights of ingredients a) to d) in the composition adds up to at least 98%) of the composition's weight,
wherein said composition contains a mixture of PPG-3 myristyl ether together with isocetyl alcohol and neopentyl glycol diethylhexanoate,
wherein the weight concentration of PPG-3 myristyl ether is 50% of the combined weight of the mixture and the other two components thereof are present in equal weight % amounts in the mixture.

17. A composition consisting of:
a) a fragrance component, in an amount of between 3 and 40% by weight of the composition's weight, at least 40% by weight of the total weight of said fragrance component being formed of perfuming ingredients having a calculated vapor pressure V comprised in the range $0.05<V<300$ Pa;
b) from 40 to 90% by weight, relative to the total weight of the composition, of ethanol;
c) from 0.01 to 20% by weight, relative to the total weight of the composition, of a fragrance modulator comprising PPG-3 myristyl ether, provided that said fragrance modulator comprises less than 50% by weight of isocetyl alcohol and less than 50% by weight of neopentyl glycol diethylhexanoate; and
d) optionally water;
wherein the sum of the weights of ingredients a) to d) in the composition adds up to at least 98%) of the composition's weight,
wherein said composition contains a mixture of PPG-3 myristyl ether together with isocetyl alcohol and neopentyl glycol diethylhexanoate,
wherein the weight concentration of PPG-3 myristyl ether is 50% of the combined weight of the mixture and the other two components thereof are present in equal weight % amounts in the mixture.

* * * * *